United States Patent [19]

Imanari et al.

[11] Patent Number: 4,906,791
[45] Date of Patent: Mar. 6, 1990

[54] PROCESS FOR PREPARING P-CUMYLPHENOL

[75] Inventors: Makoto Imanari; Hiroshi Iwane; Takahiro Sugawara; Satoshi Ohtaka, all of Ibaraki; Masashi Inaba; Mitsugi Kataoka, both of Mie, all of Japan

[73] Assignee: Mitsubishi Petrochemical Co., Ltd., Tokyo, Japan

[21] Appl. No.: 232,956

[22] Filed: Aug. 16, 1988

[51] Int. Cl.$^4$ .................. C07C 39/14; C07C 39/11
[52] U.S. Cl. ....................................................... 568/744
[58] Field of Search ........................ 568/744, 780, 790

[56] References Cited

U.S. PATENT DOCUMENTS

| | | | |
|---|---|---|---|
| 2,028,043 | 1/1936 | Britton et al. | 568/744 |
| 3,367,981 | 2/1968 | Napolitano | 568/744 |
| 3,642,926 | 2/1972 | Chapman et al. | 568/744 |

FOREIGN PATENT DOCUMENTS 831828  5/1957  United Kingdom ................ 568/744

*Primary Examiner*—Werren B. Lone
*Attorney, Agent, or Firm*—Oblon, Spivak, McClelland, Maier & Neustadt

[57] ABSTRACT

A process for preparing p-cumylphenol which comprises reacting phenol and α-methylstyrene in the presence of an inorganic solid acid catalyst having an acid point of an acid strength Ho of up to −3, for example, activated clay and recovering the aimed p-cumylphenol from the reaction mixture thus obtained by distilling the same while introducing an inert gas such as nitrogen and/or steam into the distillation system is disclosed. The p-cumylphenol thus obtained has a high purity and an improved color compared with those obtained by conventional methods.

7 Claims, No Drawings

PROCESS FOR PREPARING P-CUMYLPHENOL

FIELD OF THE INVENTION

This invention relates to a process for preparing p-cumylphenol by reacting α-methylstyrene with phenol in the presence of a catalyst.

According to the present invention, highly pure p-cumylphenol, which is useful as intermediate of, for example, bactericides, nonionic surfactants, antioxidants and resins, can be prepared at a high yield.

BACKGROUND OF THE INVENTION

Known methods for preparing p-cumylphenol from α-methylstyrene and phenol include, for example, the one described in U.S. Pat. No. 2,882,322 which comprises reacting phenol and α-methylstyrene in the presence of sulfuric acid as a catalyst. However, this method has some disadvantages. For example, it gives only a limited yield or it requires a troublesome operation for the removal of the sulfuric acid catalyst. It is further required to remove light-boiling substances including phenol and heavy-boiling substances including colored materials from the reaction mixture in order to obtain the aimed p-cumylphenol product. When distillation is used for purification processes, it easily causes thermal decomposition of the p-cumylphenol into α-methylstyrene and phenol during the distillation, even though the acid catalyst was sufficiently removed before distillation. Therefore the obtained product is contaminated with these by-products and it is thus required to purify the same by recrystallization in order to obtain p-cumylphenol of a high purity. This crystalization step makes the procedure complicated and expensive, such that, it is required to recycle a solvent used in this step.

Japanese Patent Publication No. 30614/75 has proposed a process for preparing p-cumylphenol by reacting phenol and α-methylstyrene in the presence of a sulfonated cation exchange resin catalyst which can be readily removed after the reaction. However this process is accompanied by some troubles such that the ion exchange resin is expensive and that sulfonate ion would be eluted into the reaction mixture. There is merely disclosed in this patent that the aimed p-cumylphenol can be isolated from the reaction mixture by distillation or crystallization, but there is not specifically disclosed therein that the reaction mixture can be distilled to thereby give the aimed p-cumylphenol of a high purity.

Further a process wherein a reaction mixture containing p-cumylphenol is distilled at a low temperature under high vacuum condition to thereby prevent the thermal decomposition of the p-cumylphenol during the distillation is extremely disadvantageous from an industrial viewpoint, since the vapor pressure of p-cumylphenol is low and thus it requires the high degree of vacuum up to 10 mmHg in order to conduct the distillation at a temperature of up to 180° C.

SUMMARY OF THE INVENTION

Under these circumstances, we have attempted to overcome these disadvantages of the prior arts and consequently completed the present invention.

Accordingly, the present invention provides a process for preparing p-cumylphenol by reacting phenol and α-methylstyrene in the presence of a catalyst, wherein the catalyst is an inorganic solid acid catalyst having an acid point of an acid strength Ho of up to −3.

The present invention further provides a process for preparing p-cumylphenol of a high purity which comprises distilling a composition containing p-cumylphenol which is obtained by reacting phenol and α-methylstyrene. Namely, the second aspects of the present invention enables to efficiently and readily prepare a highly pure p-cumylphenol product with high yield by a process comprising distilling a composition containing p-cumylphenol to thereby isolate the p-cumylphenol, wherein the distillation is carried out while introducing an inert gas into the distillation system.

The process of the present invention wherein an inorganic solid acid catalyst is employed can suppress the formaton of α-methylstyrene dimers by-product and thus elevate the yield of the aimed p-cumylphenol. Further, the catalyst can be readily removed since it is insoluble in the reaction mixture. Accordingly, the distillation can be carried out without requiring any specific operation such as the removal of the catalyst by washing the reaction mixture. In addition, the contamination of the product with a trace amount of phenol and α-methylstyrene formed during the distillation can be prevented by introducing an inert gas into the distillation system, which makes it possible to readily obtain p-cumylphenol of a high purity.

DETAILED DESCRIPTION OF THE INVENTION

Inorganic solid acid catalyst

The inorganic solid acid catalyst to be used in the process of the present invention should have an acid point of an acid strength Ho of up to −3. In the present invention, the term "acid strength Ho" is defined as the capability of providing a proton to a base or receiving a electron pair and is determined by using various acid-base indicators of known pka's (cf. K. Tanabe and T. Takeshita, "San Enki Shokubai", pp. 161–162 (1966), Sangyo Tosho).

Examples of the inorganic solid acid catalyst having an acid point of an acid strength Ho of up to −3 include composite oxides such as silica/alumina, various zeolites, titania/silica, titania/zirconia and magnesia/silica, mineral clays such as activated clay, bentonite and kaolin, mounted acids prepared by depositing sulfuric acid or phosphoric acid, for example, on silica gel or alumina, fixed compounds such as metal sulfates, metal phosphates and metal halides and heteropolyacid.

In addition to these inorganic solid acid catalysts, those having an acid point of an acid strength of up to −3 described in "San Enki Shokubai", p. 160 as cited above as well as in T. Shimizu, "Kinzoku Sankabutsu to sono Shokubai Sayo", p. 103 (1978), Kodansha are also available.

Among these inorganic solid acid catalysts, activated clay is the most preferable.

Reaction Method

The reaction may be carried out in either a batchwise system with the use of a stirring vessel or a continuous system with the use of a fixed-bed reactor.

The molar ratio of the phenol to the α-methylstyrene is not particularly restricted. But, it is generally preferable to use 0.5 to 6 mols of phenol per mol of α-methylstyrene. Although the reaction would proceed with the use of 6 mols or more of phenol per mol of α-methylstyrene, it is required to recover a large amount of phenol in this case. Thus it is not preferable from a practical viewpoint. When the amount of the phenol to be used is too small, on the other hand, the amount of the formed α-methylstyrene dimers is increased, which lowers the yield of the aimed product. When the reaction is carried out batchwise in a stirring vessel, it is preferable to first feed phenol and a catalyst to the reactor and then successively feed α-methylstyrene thereto. When the reaction is carried out by a fixed-bed continuous reactor, it is preferable to divide the reaction bed into the several parts and to feed α-methylstyrene stepwise to each part to thereby achieve high selectivity.

The reaction may be carried out at a temperature of 30° to 200° C., preferably 50° to 120° C. When the reaction is carried out batchwise, the catalyst may be employed in an amount of 0.1 to 50% by weight, preferably 1 to 20% by weight, based on the phenol. The reaction period generally ranges from 3 to 10 hours, although it varies depending on the reaction temperature and on the amount of the catalyst. When the reaction is carried out continuously, the liquid space velocity ranges from 0.1 to 10 per hour, preferably 0.2 to 5 per hour.

Reaction product

In addition to the main product p-cumylphenol, o-cumylphenol and α-methylstyrene dimers are formed as by-products by this reaction. The α-methylstyrene dimers include 1,1,3-trimethyl-3-phenylindane, 2,4-diphenyl-4-methyl-1-pentene and 2,4-diphenyl-4-methyl-2-pentene. Among these dimers, 2,4-diphenyl-4-methyl-1-pentene and 2,4-diphenyl-4-methyl-2-pentene can be converted into the aimed p-cumylphenol by sufficiently prolonging the reaction period (cf. K. Zicborak, W. Ratajczak and H. Kowalska, Chemia Stosowana, 26, p. 341 (1982)).

In order to isolate and purify the aimed p-cumylphenol from the reaction mixture, the catalyst is removed by, for example, filtering and then the filtrate is distilled.

The distillation process may be divided into the first distillation step whereby the unreacted phenol and α-methylstyrene are recovered, the second distillation step whereby the light-boiling by-products such as o-cumylphenol and α-methylstyrene dimers are removed and the third distillation step whereby the aimed p-cumylphenol is isolated. The distillation may be carried out either batchwise or continuously. In order to prevent the thermal decomposition of the aimed product, it is generally carried out under reduced pressure. The column-bottom temperature during the distillation may be up to 300° C., preferably up to 250° C. When the distillation temperature is excessively high, p-cumylphenol is thermally decomposed, which lowers the yield of the product. The cooling temperature of the reflux condenser is not particularly restricted so long as it exceeds the melting point of p-cumylphenol (72° C.). It preferably ranges from 75° to 150° C.

In the second aspect of the present invention, an inert gas is introduced into the distillation system during the above described third distillation step for the isolation of the aimed p-cumylphenol and the p-cumylphenol is distilled under the inert gas stream. Thus, the contamination of the aimed product with a trace amount of phenol and α-methylstyrene, which are formed by the thermal decomposition of the p-cumylphenol during the distillation, can be substantially prevented, which enables to obtain the p-cumylphenol at a extremely high purity. During the third distillation step, the column-bottom temperature is adjusted to 180° to 300° C., preferably to 200° to 250° C. The inert gas to be introduced is not particularly restricted so long as it is inert to the materials to be distilled. Examples thereof include nitrogen, carbon dioxide, helium and argon. Nitrogen is readily available and thus particularly preferable.

Alternatively, steam may be used as the inert gas. When steam is to be used, the moisture content of the product can be lowered by controlling the temperature of the condenser to at least 100° C.

The inert gas may be introduced to, for example, the bottom of the column including the reboiler, the medium thereof, the top thereof, the reflux condenser or the reflux drum. The highest effect can be achieved by introducing the inert gas to the bottom of the column or to the medium thereof.

The inert gas is continuously mixed with the p-cumylphenol vapor rising in the column to thereby inhibit the condensation of the α-methylstyrene and phenol within the condenser. Thus the contamination of the aimed p-cumylphenol with the α-methylstyrene and phenol can be suppressed.

The inert gas may be introduced into the column in an amount of 0.001 to 1.0 mol, preferably 0.005 to 0.1 mol, per mol of the rising vapor therein other than the same.

When the amount of the inert gas is too small, the phenol and α-methylstyrene can be scarcely removed. When it is too large, on the other hand, the degree of vacuum within the column might be lowered, the purifying effect of the distillation might be damaged or the yield of the p-cumylphenol might be lowered.

According to the process of the present invention, a highly pure p-cumylphenol product can be readily obtained. In addition, the product thus obtained has an improved color compared with those obtained by conventional methods.

The present invention will be explained in greater detail with reference to the following examples, but the present invention should not be construed as being limited thereto.

EXAMPLE 1

18.8 g (200 mmols) of phenol and 0.38 g (2% by weight of the phenol) of Silton CS-1 (activated clay manufactured by Mizusawa Kagaku K.K.) were fed into a reactor provided with a stirrer, a dropping funnel and a thermometer and heated to 80° C. therein under stirring. Then 11.8 g (100 mmols) of α-methylstyrene was successively added thereto within 6 hours and the obtained mixture was further reacted for additional 1 hour. The acid strength of the activated clay determined by Hammett's indicator was as follows:

$$-5.6 < Ho \leq -3.$$

The reaction mixture was cooled to room temperature and the activated clay was filtered off. The filtrate was analyzed by gas chromatography. As a result, the conversion of the α-methylstyrene was 100% and the yield of the p-cumylphenol based on the α-methylstyrene was 93%. In addition, 1.8% of o-cumylphenol and 2.9% of o-methylstyrene dimers were formed.

EXAMPLE 2

The procedure of Example 1 was repeated except that the Silton CS-1 was replaced with "Kassei Hakudo" (activated clay manufactured by Nippon Kassei Hakudo K.K.: $-8.2 < Ho \leq -5.6$). The conversion of the α-methylstyrene was 100% and the yield of the p-cumylphenol based on the α-methylstyrene was 87%.

EXAMPLE 3

1,034 g (11 mols) of phenol and 9.2 g of Silton CS-1 were fed into a glass stirring tank. 590 g (5 mols) of α-methylstyrene was successively added thereto within 6 hours at 80° C. After the completion of the addition, the obtained mixture was further reacted for additional 1 hour. The reaction mixture was filtered to thereby remove the catalyst and the filtrate was analyzed. As a result, it contained 59.3% by weight of p-cumylphenol, 34.3% by weight of unreacted phenol, up to 0.1% by weight of unreacted α-methylstyrene, 4.5% by weight of α-methylstyrene dimers and 1.8% by weight of other components.

1.5 kg of the above reaction mixture was fed into the bottom of a glass batch distillation apparatus (column diameter: 40 mm) provided with a refluxing device on the column top and packed with a stainless packing corresponding to theoretical plate number of 20. Then the mixture was distilled under reduced pressure while introducing 2.7 Nl/hr (0.12 mol/hr) of nitrogen gas through a capillary into the tower bottom. The distillation was carried out at a constant reflux ratio of 5.0 under constant pressure of approximately 30 mmHg at the bottom. The vapor velocity within the column was approximately 3 mol/hr and the bottom temperature was 220° C. while distilling the p-cumylphenol product. Thus 0.71 kg of the aimed fraction was obtained (yield of p-cumylphenol: 80%). This fraction was analyzed by gas chromatography. As a result, the purity of the p-cumylphenol was 99.95%. The molten color of the product was less than APHA 10. Table 1 shows the composition.

EXAMPLE 4

The procedure of Example 3 was repeated except that not the nitrogen but steam was introduced to the tower bottom at a rate of 0.6 mol/hr during the distillation. Thus 0.71 kg of the aimed fraction was obtained (yield of p-cumylphenol: 80%). Table 1 shows the results.

EXAMPLE 5

32 kg of phenol and 640 g of Silton CS-1 were fed into a stainless reactor (volume: 100 l) and heated to 75° C. 18.8 kg of α-methylstyrene was successively added thereto within 7 hours and the obtained mixture was further reacted for additional 1 hour. The reaction mixture was cooled and the catalyst was filtered off. Then the filtrate was analyzed by gas chromatography. As a result, it contained 60.9% by weight of p-cumylphenol, 34.8% by weight of unreacted phenol, up to 0.1% by weight of unreacted α-methylstyrene, 2.6% by weight of α-methylstyrene dimers and 1.6% by weight of other components.

38 kg of the composition containing p-cumylphenol, as obtained above, was fed into a bottom of a stainless batch distillation apparatus (bottom volume: 50 l, column diameter: 3 inch) provided with a nitrogen-introducing nozzle (capable of introducing nitrogen gas to the gas phase in the tower bottom) and packed with a stainless packing corresponding to a theoretical plate number of 30. The composition was distilled while introducing 27 Nl/hr (1.2 mol/hr) of nitrogen gas through the nozzle into the tower bottom under reduced pressure. The distillation was carried out at a constant reflux ratio of 5.0 under a constant pressure of approximately 30 mmHg at the tower bottom. The vapor velocity within the column during the distillation was approximately 17 mol/hr and the bottom temperature was 220° C. during the distillation of the main component. Thus 18.1 kg of the aimed fraction (yield of p-cumylphenol: 78%) was obtained. The purity of the p-cumylphenol was 99.95% and the molten color thereof was less than APHA 10. Table 1 shows the results.

REFERENTIAL EXAMPLE 1

The procedure of Example 5 was repeated except that no nitrogen was introduced during the distillation. Thus 17.6 kg of the aimed fraction was obtained (yield of p-cumylphenol: 76%). Table 1 shows the results.

REFERENTIAL EXAMPLE 2

The procedure of Example 5 was repeated except that no nitrogen was introduced during the distillation and the tower bottom pressure during the distillation was maintained at a constant level of approximately 20 mmHg. The bottom temperature during the distillation of the main component was 205° C. Thus 17.5 kg of the aimed fraction was obtained (yield of p-cumylphenol: 76%). Table 1 shows the results.

TABLE 1

|  | Vapor velocity (mol/hr) | Amount of inert gas | (mol/hr) | Composition of aimed fraction* (% by weight) | | | | |
|---|---|---|---|---|---|---|---|---|
|  |  |  |  | α-MS | PL | α-MSD | PCP | Others |
| Example 3 | ca. 3.0 | N$_2$ | 0.12 | 0.004 | t. | 0.009 | 99.974 | 0.013 |
| Example 4 | " | H$_2$O | 0.6 | t. | t. | 0.010 | 99.975 | 0.015 |
| Example 5 | ca. 1.70 | N$_2$ | 1.2 | 0.011 | 0.008 | 0.009 | 99.958 | 0.014 |
| Referential Example 1 | " | — |  | 0.185 | 0.127 | 0.015 | 99.648 | 0.025 |
| Referential Example 2 | " | — |  | 0.097 | 0.067 | 0.016 | 99.796 | 0.024 |

Note:
α-MS: α-methylstyrene.
PL: phenol.
α-MSD: α-methylstyrene dimers.
PCP: p-cumylphenol.
t: trace.

What is claimed is:

1. A process for preparing p-cumylphenol which comprises reacting phenol and α-methylstyrene in the presence of an inorganic solid acid catalyst, at a temperature of 30° to 200° C., and isolating said p-cumylphenol from the reaction mixture thus obtained by distilling said p-cumylphenol while introducing an inert gas into the distillation system, wherein said distillation system includes a reboiler, a still, a column, a reflux condenser, and a reflux drum, and wherein the column-bottom temperature at the isolation of said p-cumylphenol is maintained at a temperature of from 180° to 300° C.

2. A process for preparing p-cumylphenol as claimed in claim 1, wherein said acid catalyst is an inorganic solid acid catalyst having an acid point of an acid strength Ho of up to $-3$.

3. A process for preparing p-cumylphenol as claimed in claim 1, wherein said inert gas is at least one selected from among nitrogen and steam.

4. A process for preparing p-cumylphenol as claimed in claim 1, wherein said inert gas is introduced in an amount of 0.001 to 1.0 mol per mol of the rising vapor other than the same in the distillation system.

5. The process of claim 1, wherein said inorganic solid acid catalyst has an acid point of an acid strength $H_o$ of up to $-3$.

6. The process of claim 1, wherein said inorganic solid acid catalyst is activated clay.

7. The process of claim 6, wherein said activated clay is present in an amount of 0.1 to 50% by weight based on phenol.

* * * * *